United States Patent
Berg

(10) Patent No.: US 6,932,765 B2
(45) Date of Patent: Aug. 23, 2005

(54) APPARATUS FOR RETAINING OTHERWISE HAND-HELD RETRACTORS

(75) Inventor: Christopher Lee Berg, Crystal, MN (US)

(73) Assignee: Minnesota Scientific, Inc., St. Paul, MN (US)

( * ) Notice: Subject to any disclaimer, the term of this patent is extended or adjusted under 35 U.S.C. 154(b) by 0 days.

(21) Appl. No.: 10/936,865

(22) Filed: Sep. 9, 2004

(65) Prior Publication Data

US 2005/0033118 A1 Feb. 10, 2005

Related U.S. Application Data

(63) Continuation of application No. 10/057,840, filed on Oct. 26, 2001, now abandoned.

(51) Int. Cl.[7] .................................................. A61C 1/32
(52) U.S. Cl. ........................ 600/231; 600/233; 600/232
(58) Field of Search ................................ 600/231, 232, 600/233, 227

(56) References Cited

U.S. PATENT DOCUMENTS

| | | | |
|---|---|---|---|
| 2,313,164 A | 3/1943 | Nelson | 128/20 |
| 3,782,370 A | 1/1974 | McDonald | 128/20 |
| 3,844,550 A | 10/1974 | McGuire | 269/328 |
| 4,350,151 A | 9/1982 | Scott | 600/225 |
| RE32,021 E | 11/1985 | Scott, Jr. | 600/217 |
| 4,827,926 A | 5/1989 | Carol | 128/303 |
| 4,950,222 A | 8/1990 | Scott et al. | 600/21 |
| 5,104,103 A | 4/1992 | Auchinleck et al. | 269/74 |
| 5,307,790 A | 5/1994 | Byrne | 128/20 |
| 5,728,041 A | 3/1998 | Fowler, Jr. | 600/21 |
| 5,728,047 A | 3/1998 | Edoga | 600/227 |
| 5,755,661 A | 5/1998 | Schwartzman | 600/216 |
| 5,769,783 A | 6/1998 | Fowler | 600/226 |
| 5,785,649 A | 7/1998 | Fowler, Jr. | 600/233 |
| 5,857,965 A | 1/1999 | Rootman et al. | 600/233 |
| 5,899,425 A | 5/1999 | Corey, Jr. et al. | 248/276.1 |
| 5,899,853 A | 5/1999 | Fowler, Jr. | 600/217 |
| 5,954,639 A | 9/1999 | Gray | 600/233 |
| 5,964,697 A | 10/1999 | Fowler, Jr. | 600/210 |
| 5,964,698 A | 10/1999 | Fowler | 600/217 |
| 6,077,221 A | 6/2000 | Fowler, Jr. | 600/233 |
| 6,090,043 A | 7/2000 | Austin et al. | 600/217 |
| 6,102,922 A | 8/2000 | Jakobsson et al. | 606/157 |
| 6,117,072 A | 9/2000 | Fowler, Jr. | 600/217 |
| 6,190,312 B1 | 2/2001 | Fowler, Jr. | 600/231 |
| 6,468,207 B1 | 10/2002 | Fowler, Jr. | 600/233 |
| 6,709,389 B2 | 3/2004 | Farascioni | 600/229 |

Primary Examiner—Cary E. O'Connor
Assistant Examiner—Candice C. Stokes
(74) Attorney, Agent, or Firm—Westman, Champlin & Kelly, P.A.

(57) ABSTRACT

A retractor retaining device retains an otherwise handheld retractor in the retraction position. The device includes a flexible loop that is detachably attached to a retractor support proximate the surgical wound with the loop engaging a proximal end or handle of the retractor to retain the retractor in the retraction position.

36 Claims, 3 Drawing Sheets

APPARATUS FOR RETAINING OTHERWISE HAND-HELD RETRACTORS

CROSS-REFERENCE TO RELATED APPLICATIONS(S)

The present application is a continuation of and claims priority of U.S. patent application Ser. No. 10/057,840, filed Oct. 26, 2000 now abandoned, the content of which is hereby incorporated by reference in its entirety.

BACKGROUND OF THE INVENTION

The present invention relates to surgical retractors, and to devices for holding surgical retractors in a retraction position.

Most improvements in surgical retractor supports or clamps to hold surgical retractors in a retraction position are directed to improvements on devices that have been used to mount retractors on retractor supports using rigid mechanical clamps for restraints. However, in certain situations, retractors are still manually held by a nurse or a surgeon since no clamp provides such versatile holding characsteristics. There are no devices that will retain a retractor in the retraction position that is otherwise manually held from a typical retractor support. The Edoga U.S. Pat. No. 5,728,047 describes the use of a belt on which various types of retractor retaining mechanism are shown, especially in FIGS. 7a through 7i. However, these retaining mechanisms do not address the problem of quickly and easily retaining an otherwise manually held retractor. Furthermore, the retractor handle has to be specially adapted to engage the fastening mechanism.

BRIEF SUMMARY OF THE INVENTION

The present invention includes a retractor retaining device for retaining a retractor in a retraction position within a surgical wound from a retractor support. The retractor retaining device includes a main body that is attachable to the retractor support and a flexible loop that is detachably attached to the main body for engaging a proximal end of the tractor such that the retractor is retained in the retraction position.

The invention also includes a method of holding a surgical retractor in the retraction position within the surgical wound. The method includes providing a support member near the surgical wound and then inserting a retractor within the surgical in a retraction position. The retractor is retained in the retraction position by securing a proximal end of the retractor in engagement with a flexible loop that is attached to the support member thereby securing the retractor in the retraction position.

DETAILED DESCRIPTION

Figure 1:
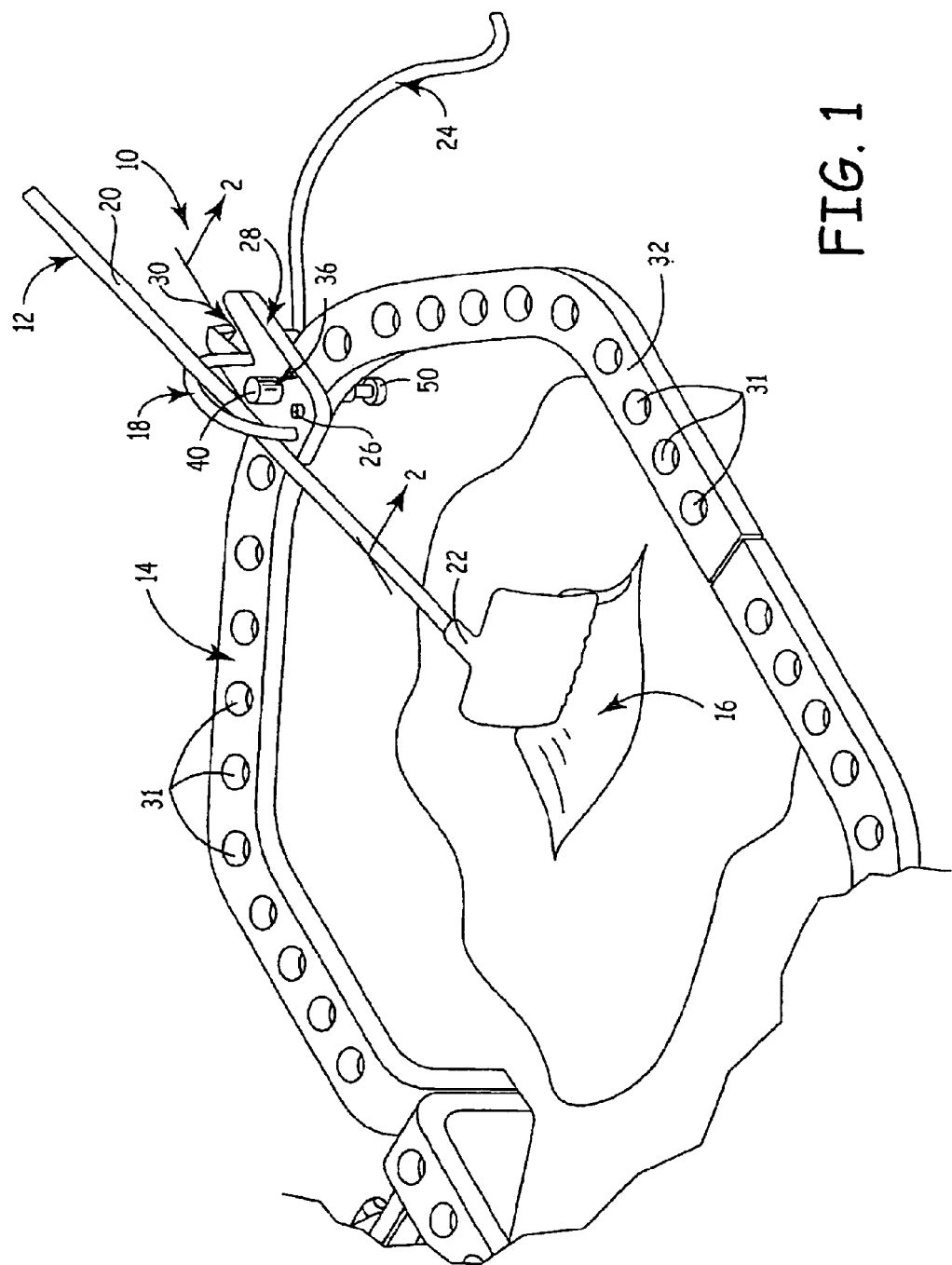
FIG. 1 is a perspective view of the present invention in use.

The retractor retaining device of the present invention is generally indicated at 10 in FIG. 1. Like reference characters will be used to indicate like elements throughout the drawings. The device 10 retains a retractor 12 in a retraction position. The device 10 is used for retaining retractors that are otherwise manually held in the retraction position. The retractor 12 is initially manually placed in the retraction position and the device 10 is then used to retain the retractor 12 which otherwise would have to be held in a retraction position manually by a doctor or a nurse.

The device 10 is mounted on a retractor support 14 that is positioned over or proximate to a surgical wound 16. The type of retractor support 14 is not particularly important to the present invention except that it provides a solid base to which the retaining device 10 is attached.

The essence of the present invention is to provide a structure and a method for retaining the retractor 12 that is normally held in a retraction position manually. The device 10 quickly engages the retractor or is quickly disengaged from the retractor. The retractor does not require a handle designed to be gripped by a specific retaining device and can therefore be of any shape. This purpose is accomplished by providing a loop 18 that extends from the support 14 and encircles a proximal end (handle) 20 of the retractor 12. The retractor 12 at a distal end is inserted into the wound 16. The loop 18 encircles the proximal end 20 of the retractor 12 securing the retractor 12 in a retraction position.

The loop 18 is a portion of cord 24. The cord 24 is secured at a first end 26 to a platform 28 of the retaining device 10. Preferably, the length or size of the loop 18 is adjustable. For adjustability, the cord 24 is detachably attachable to the platform 28 in a quick connect/disconnect fashion. The detachable attachment serves at least two purposes. The first is that the size of the loop 18 is thereby adjustable to accommodate different diameters of retractor handle 20, and second to quickly and easily encircle the handle 20 with the cord 24.

A preferred method of quickly detachably attaching the cord 24 to the platform 28 includes a V-shaped notch 30 in the platform 28. The cord 24 is secured by positioning the cord 24 into the V-shaped notch 30 with the V-shaped notch 30 engaging the cord 24 as the cord is pulled into a progressively smaller area of the V-shaped notch 30.

Figure 2:
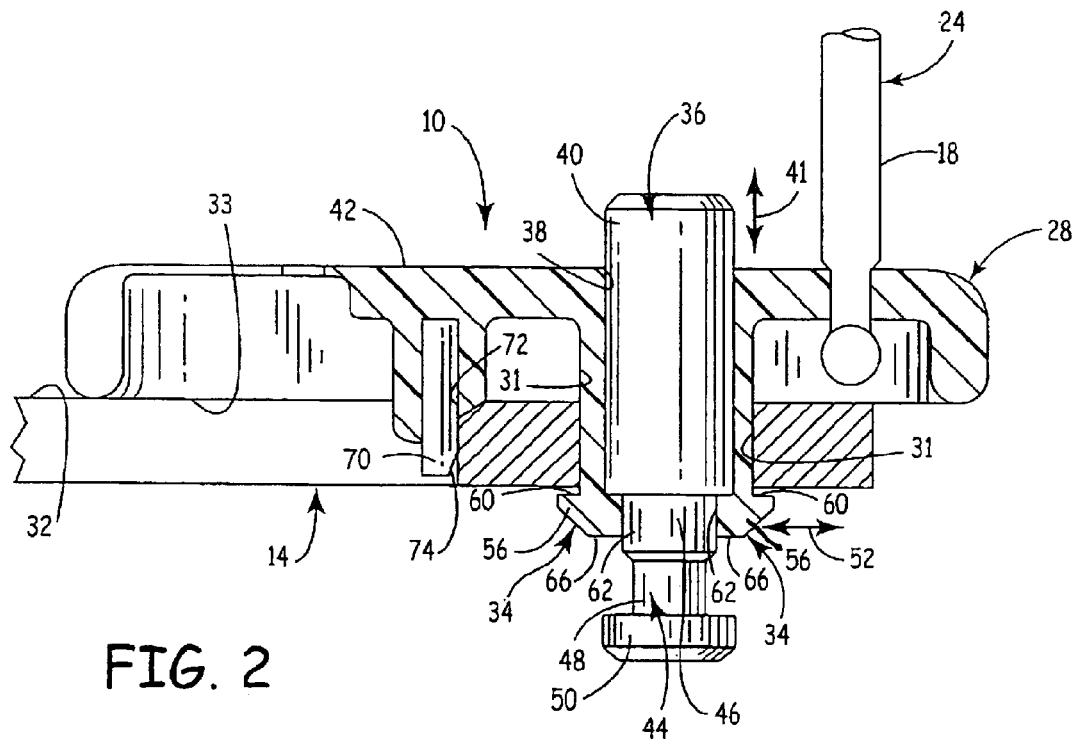
FIG. 2 is a cross-sectional view taken along the lines 2—2 in FIG. 1.
Figure 3:
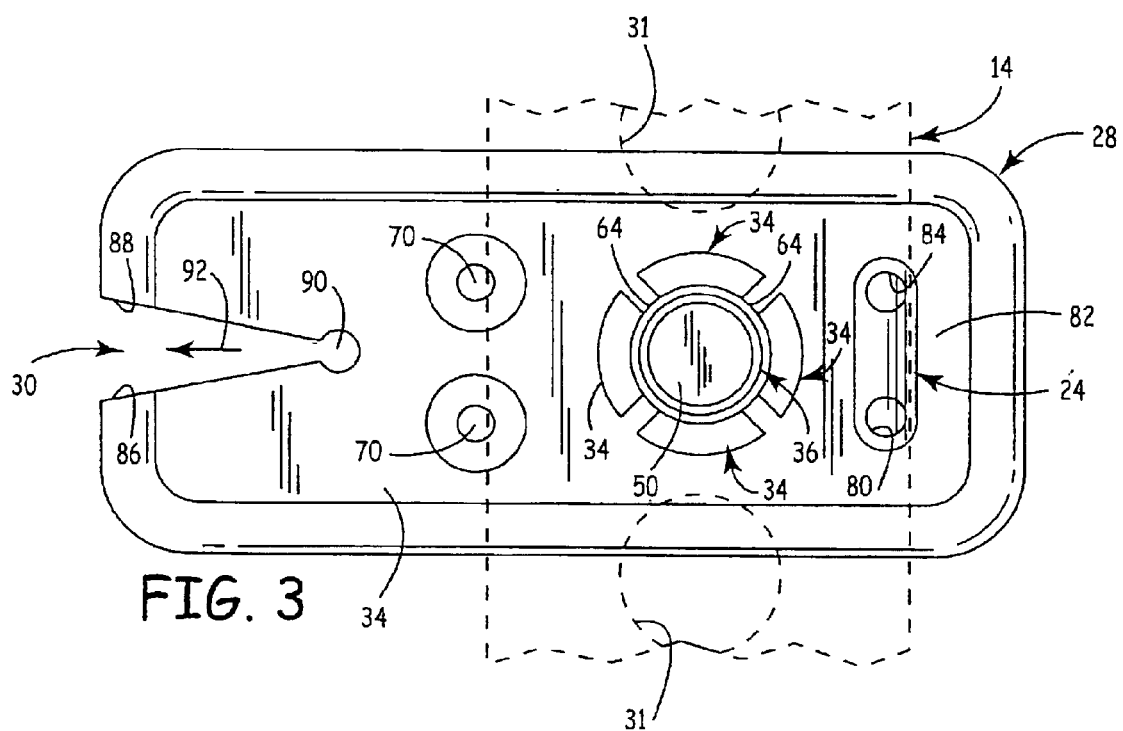
FIG. 3 is a bottom view of one embodiment of the device in the present invention.

The retaining device 10 is preferably configured to engage apertures 30 in the retractor support member 14. Preferably, the retractor support 14 has an upper surface 32 that is substantially flat and is disposed in an horizontal position proximate the wound 16. The platform 28 of the retaining device 10 includes a correspondingly lower substantially flat surface 34 as best illustrated in FIG. 2. The platform 28 includes a plurality of resilient fingers 34 as best illustrated in FIGS. 2 and 3 that extend into one of the apertures 30 for securing the platform 28 to the support member 14. The embodiment 10 includes preferably four fingers as best illustrated in FIG. 3. A button member 36 extends into a bore 38 and moves within the bore 38 in the direction indicated by arrows 40 in FIG. 2. The button member 36 has an upper portion 40 extending above an upper surface 42 of the platform 28 such that the upper surface is engageable by a finger or thumb. At a lower portion 44, the button member 36 has a first reduced diameter section 46 that has a smaller diameter than the upper portion 40 and a second lower section of reduced diameter 48 that has a smaller diameter than the section 46 and an end portion 50 disposed below and adjacent to section 48 and having a diameter larger than the sections 46 and 48.

The resilient fingers 34 flex in a direction indicated by arrows 52. Each finger 34 includes an upper finger section 54 that when extended into the aperture 30 is spaced therefrom to permit flexing. The fingers 34 also each have a lower section 56 that is set apart from the upper section 54 by an inwardly extending sloped shoulder 58 and an outwardly extending shoulder 60. The inwardly extending sloped shoulder 58 extends sufficiently inward such that the upper portion 40 of the button member 36 cannot be moved past inwardly facing surfaces 62 of the lower section 56 of the finger 34. The inwardly facing surfaces 62 of each of the fingers 34 collectively form a through hole 64 through which the lower portion 44 of the button member 36 is disposed and moves therethrough in a direction of arrow 41. The end portion 50 is positioned below the through hole 64 and has a diameter that is larger than the lower portion 44 and larger than the through hole 64 such that the end portion 50 acts as a stop when the button member is pushed upwardly in one of the directions indicated by arrow 40 and abuts against a lower surface 66 of each of the fingers 34.

In operation, to secure the device 10 to the support member 14, the fingers 34 are inserted into the aperture 30 with the button member at its uppermost position, that is the end portion 50 abutting against the lower surfaces 66 of the fingers 34. To secure the device 10 to the support member 14, the button member is engaged manually at its upper end 40 and pushed in a downward direction as indicated by arrow 41. When moved in the downward direction, the end 40 and section 46 act against the inwardly extending sloped shoulders 58 of the fingers 34 thereby flexing the fingers in a radial outward direction as indicated by arrow 52. The outwardly flexing of the resilient fingers engages the outwardly extending shoulders 60 with a lower surface of the support member 14 securing the device 10 to the support member 14.

To disengage the device 10 from the support member 14, the lower end 50 is pushed manually in an upward direction as indicated by arrow 40 thereby removing the section 46 from engagement with the inwardly extending sloped shoulders 58 of the resilient fingers 34 thereby permitting the lower portions of the fingers 34 to extend radially inwardly such that the outwardly extending shoulders 60 are removed from engagement with the lower surface of the support member 14.

Additionally, to better guide the engagement of the device 10 with the support member 14, a pair of downwardly extending guide posts 70 extend downwardly from the platform 28 and engage a side surface 72 of the support member 14. The posts 70 preferably have beveled surfaces 74 to facilitate engagement of the side surface 72 of the support member 14. The guide post 70 also prevents rotational movement of the platform 28 about the aperture 30.

Figure 4:
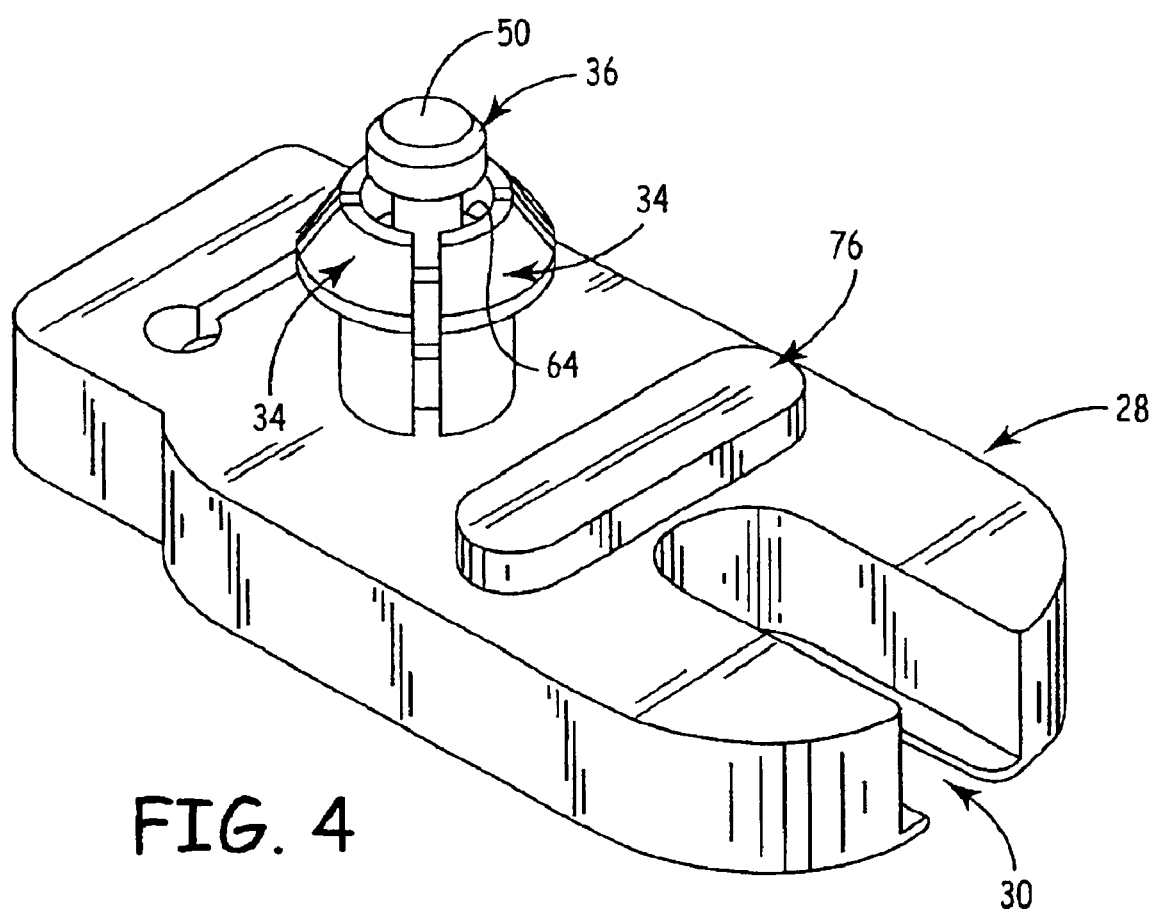
FIG. 4 is a perspective view showing the bottom surface of another embodiment of the present invention.

Another embodiment of the present invention is illustrated in FIG. 4 which includes a downwardly extending guide shoulder 76 instead of the posts 70.

The cord 24 is engaged at one end to the platform 28 by initially inserting the first end 26 into a first cord engaging aperture 80, as best illustrated in FIG. 3. The cord is then positioned along cavity 82 and the remainder of the cord is then inserted into a second cord engaging aperture 84 and pulled such that the cord is drawn taught and frictionally engaged by apertures 80 and 82. The cord 24 is made of a plastic material that is slightly compressible. The slight compressibility of cord adds to the frictional forces for engagement of the cord through its travel within apertures 80 and 84.

The slight compressibility of the cord also aids in engagement of the cord with the V-shaped notch 30. The V-shaped notch 30 has oppositely facing surfaces 86 and 88 that progressively come together until engagement aperture 90. The engagement aperture 90 is slightly less in diameter than the cord 24 such that when the cord 24 is pulled into engagement within the V-shaped notch 30, it is retained thereby in aperture 90. The cord is easily detachable from the V-shaped notch by pulling outwardly in a direction indicated by arrow 92. Thereby, the loop 18 as illustrated in FIG. 1 is quickly formed and disposed about the handle 20 of the retractor 12 and is made to fit the size of the retractor handle.

Although the present invention has been described with reference to preferred embodiments, workers skilled in the art will recognize that changes may be made in form and detail without departing from the spirit and scope of the invention.

What is claimed is:

1. A retractor retaining device for retaining a retractor from a retractor support in a retraction position within a surgical wound, the device comprising:
    a main body attachable to the retractor support; and
    a flexible loop detachably attached at one end to the main body for engaging a proximal end of the retractor such that the retractor is retained in the retraction position.

2. The device of claim 1 wherein the flexible loop is attached such that the loop may be adjusted in size for engaging the proximal end of the retractor.

3. The device of claim 1 and further including an attaching mechanism that engages and attaches the retaining device to the retractor support.

4. The device of claim 3 wherein the retractor support has a plurality of apertures and the attaching mechanism has an aperture engaging member for engaging one of the apertures.

5. The device of claim 4 wherein the aperture engaging member has a plurality of resilient fingers that are insertable into the one of the apertures to engage surfaces of the one aperture.

6. The device of claim 5 wherein the fingers define a bore and the attaching mechanism has a peg movable within the bore and wherein the peg moves the resilient fingers in an outwardly radial direction to engage surfaces of the aperture.

7. The device of claim 1 wherein the loop includes a flexible cord fixedly attached to the main body at a first end and detachably attached to the main body at a second end such that the length of the loop is adjustable.

8. The device of claim 7 wherein the main body includes a V-type slot and wherein the second end of the loop is engageable within the V-type slot such that the second end of the cord is detachably attached to the main body.

9. A retractor support for retaining a retractor in a retraction position within a surgical wound, the support comprising:
    a support member positioned near the surgical wound; and
    a flexible loop detachably attached at least at one end to the support member and engaging a proximal end of the tractor such that the retractor is retained in the retraction position.

10. The support of claim 9 wherein the flexible loop is attached such that the loop may be adjusted in size for engaging the proximal end of the retractor.

11. The support of claim 9 and further including an attaching mechanism that engages and attaches the flexible loop to the support member.

12. The support of claim 11 wherein the support member has a plurality of apertures and the attaching mechanism has an aperture engaging member for engaging one of the apertures.

13. The support of claim 12 wherein the aperture engaging member has a plurality of resilient fingers extending into one of the apertures and engaging surfaces of the one of the apertures.

14. The support of claim 13 wherein the fingers define a bore and the attaching mechanism has a peg movable within the bore and wherein the peg moves the resilient fingers in an outwardly radial direction to engage surfaces of the aperture.

15. The support of claim 11 wherein the loop includes a flexible cord fixedly attached to the attaching mechanism at a first end and detachably attached to the attaching mechanism at a second end such that the length of the loop is adjustable.

16. The device of claim 7 wherein the attaching mechanism includes a V-type slot and wherein the second end of the loop is engageable within the V-type slot such that the second end of the cord is detachably attached to the attaching mechanism.

17. A retraction device comprising:
   a retractor support member for positioning near a surgical wound;
   a retractor having a proximal end and a distal end, the distal end for insertion into the surgical wound; and
   a flexible loop secured to the retractor support member for engaging the proximal end of the retractor in a manner that retains the retractor in a retraction position within a surgical wound.

18. The device of claim 17 wherein the flexible loop is attached such that the loop may be adjusted in size for engaging the proximal end of the retractor.

19. The device of claim 17 and further including an attaching mechanism that engages and attaches the flexible loop to the retractor support.

20. The device of claim 19 wherein the retractor support has a plurality of apertures and the attaching mechanism has an aperture engaging member for engaging one of the apertures.

21. The device of claim 20 wherein the aperture engaging member has a plurality of resilient fingers extending into the one of the apertures and engaging surfaces of one of the apertures.

22. The device of claim 21 wherein the fingers define a bore and the attaching mechanism has a peg movable within the bore and wherein the peg moves the resilient fingers in an outwardly radial direction to engage surfaces of the aperture.

23. The device of claim 17 wherein the loop includes a flexible cord fixedly attached to the attaching mechanism at a first end and detachably attached to the attaching mechanism at a second end such that the length of the loop is adjustable.

24. The device of claim 23 wherein the attaching mechanism includes a V-type slot and wherein the second end of the loop is engageable within the V-type slot such that the second end of the cord is detachably attached to the attaching mechanism.

25. A method of holding a surgical retractor in a retraction position within a surgical wound, the method comprising:
   providing a support member near the surgical wound;
   inserting a distal end of a retractor within the surgical wound and manually positioning the retractor in the retraction position; and
   securing the retractor in the retraction position by engaging a proximal end of the retractor with a flexible loop that is attached to the support member.

26. The method of claim 25 and further comprising:
   adjusting the size of the loop by disengaging one end of the loop from the support member and re-engaging the loop to the support member with a different loop length.

27. The method of claim 26 wherein the loop is engaged or disengaged by engaging a V-shaped slot.

28. The method of claim 25 wherein the loop is positioned around the proximal end of the retractor.

29. A method of retaining a surgical retractor in a selected position within a surgical wound, the method comprising:
   providing a support member near the surgical wound;
   securing a retractor retaining device having a flexible strap attached thereto onto the support member;
   positioning a distal end of the surgical retractor within the surgical wound;
   manually retracting the surgical retractor into the selected position; and
   securing the surgical retractor in the selected position by engaging a proximal end of the surgical retractor with the flexible strap.

30. The method of claim 29 and further comprising:
   retaining a first end of the flexible strap in a fixed position;
   manipulating a second free end of the flexible strap to adjust a length of the flexible strap; and
   securing a mid-portion of the loop within a V-shaped slot within the retractor retaining device by a frictional engagement wherein the frictional engagement retains the hand held retractor in the selected position.

31. The method of claim 30 and further comprising:
   disengaging the mid portion of the flexible strap from the V-shaped slot;
   adjusting a position of the surgical retractor into a second selected position;
   manipulating the second end of the flexible loop to engage the proximal end of the surgical retractor with the loop; and
   securing the mid portion of the loop within the V-shaped slot to retain the surgical retractor in the second selected position by a frictional engagement of the loop with the V-shaped slot.

32. The method of claim 29 and further comprising:
   disposing a plurality of resilient fingers extending from a main body of the retractor retaining device within an aperture in the support arm, wherein the plurality of resilient fingers define a bore;
   disposing a peg within the bore; and
   positioning the peg into an engaging position such that the resilient fingers are forced in an outwardly radial direction to engage the peg.

33. A method of reducing the number of personnel required to perform a surgical procedure, the method comprising:
   providing a support member near a surgical wound;
   securing a retractor retaining device having a flexible loop attached thereto onto the support member;
   positioning a distal end of a hand held retractor within the surgical wound;
   manually retracting the surgical retractor in a selected position; and
   securing the surgical retractor into the selected position by engaging a proximal end of the surgical retractor with the flexible loop wherein the retractor retaining device retains the surgical retractor in the selected position without aid from the personnel.

34. The method of claim 33 and further comprising:
   retaining a first end of the flexible loop in a fixed position;
   manipulating a second free end of the flexible loop to adjust a length of the flexible loop; and
   securing a mid-portion of the loop within a V-shaped slot within the retractor retaining device by a frictional engagement to retain the surgical retractor in the selected position.

35. The method of claim 34 and further comprising:
   disengaging the mid portion of the flexible loop from the V-shaped slot;
   adjusting the position of the surgical retractor into a second selected position;
   manipulating the second end of the flexible loop to engage the proximal end of the surgical retractor with the loop; and
   securing the mid portion of the loop within the V-shaped slot to retain the surgical retractor in the second selected position by a frictional engagement of the loop with the V-shaped slot.

36. The method of claim 33 and further comprising:

disposing a plurality of resilient fingers extending from a main body of the retractor retaining device within an aperture in the support arm, wherein the plurality of resilient fingers define a bore;

disposing a peg within the bore defined by the resilient fingers; and positioning the peg into an engaging position such that resilient fingers are forced in an outwardly radial direction to engage the peg.

* * * * *